United States Patent [19]
Schwartz et al.

[11] Patent Number: 5,416,575
[45] Date of Patent: May 16, 1995

[54] METHOD AND SYSTEM FOR CALIBRATING AN OPTICAL DENSITY MEASUREMENT APPARATUS

[76] Inventors: Mark Schwartz, 4089 Aberdeen Ct., Orchard Lake, Mich. 48323; Paul Millman, 201 W. 70th St., New York, N.Y. 10023

[21] Appl. No.: 970,913

[22] Filed: Nov. 3, 1992

Related U.S. Application Data

[63] Continuation-in-part of Ser. No. 793,627, Nov. 18, 1991, abandoned.

[51] Int. Cl.⁶ .............................................. G01J 1/02
[52] U.S. Cl. ...................................... 356/243; 356/432
[58] Field of Search ................ 356/243, 432, 436, 39, 356/442, 433, 434, 435, 437, 440; 128/633–635, 664–667; 359/52, 75, 79, 94, 98, 102, 106, 87; 364/413.09

[56] References Cited

U.S. PATENT DOCUMENTS

| | | | |
|---|---|---|---|
| 3,837,730 | 9/1974 | Hatfield et al. | 359/98 |
| 4,223,995 | 9/1980 | Fletcher | 356/418 |
| 4,240,711 | 12/1980 | Baur et al. | 359/98 |
| 4,472,026 | 9/1984 | Boyd et al. | 359/98 |
| 4,522,470 | 6/1985 | Iijima | 359/106 |
| 4,692,883 | 9/1987 | Nelson et al. | 364/571 |
| 4,720,787 | 1/1988 | Lipscomb | 364/413.07 |
| 4,775,237 | 10/1988 | Cioppi | 356/417 |
| 4,786,128 | 11/1988 | Birnbach | 378/85 |
| 4,876,069 | 10/1989 | Jochimsen | 356/39 |
| 4,883,963 | 11/1989 | Kemeny et al. | 250/339 |
| 4,927,266 | 5/1990 | Sugiura et al. | 356/243 |
| 4,937,764 | 6/1990 | Komatsu et al. | 356/425 |
| 4,944,578 | 7/1990 | Denison | 359/106 |
| 5,030,005 | 7/1991 | Swope et al. | 356/243 |

*Primary Examiner*—Hoa Q. Pham
*Attorney, Agent, or Firm*—Brooks & Kushman

[57] ABSTRACT

A method and system for calibrating an optical density measurement apparatus includes a graphic display module that can be modulated under control of a microcomputer. The module is preferably a matrix-array type liquid crystal display wherein individual pixels may be selectively turned on or off to achieve a desired time course of transmittance changes in order to emulate the clot signature of a standard solution. Preferably the graphic LCD module includes a portion which provides a user interface during a calibration run.

14 Claims, 7 Drawing Sheets

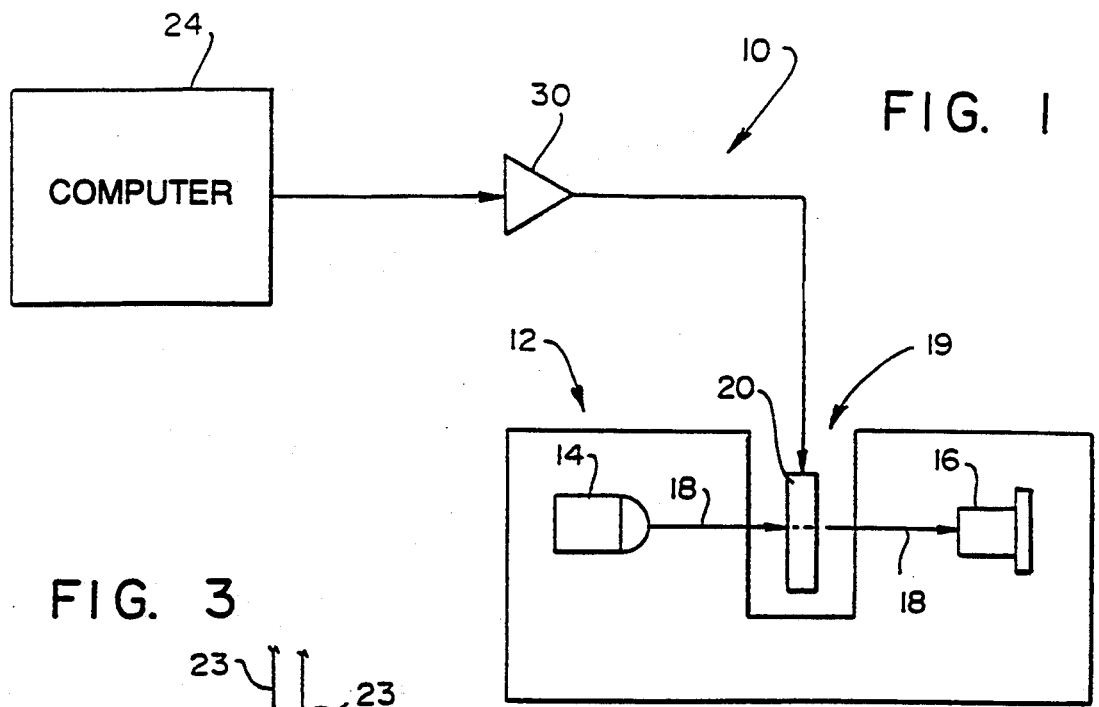
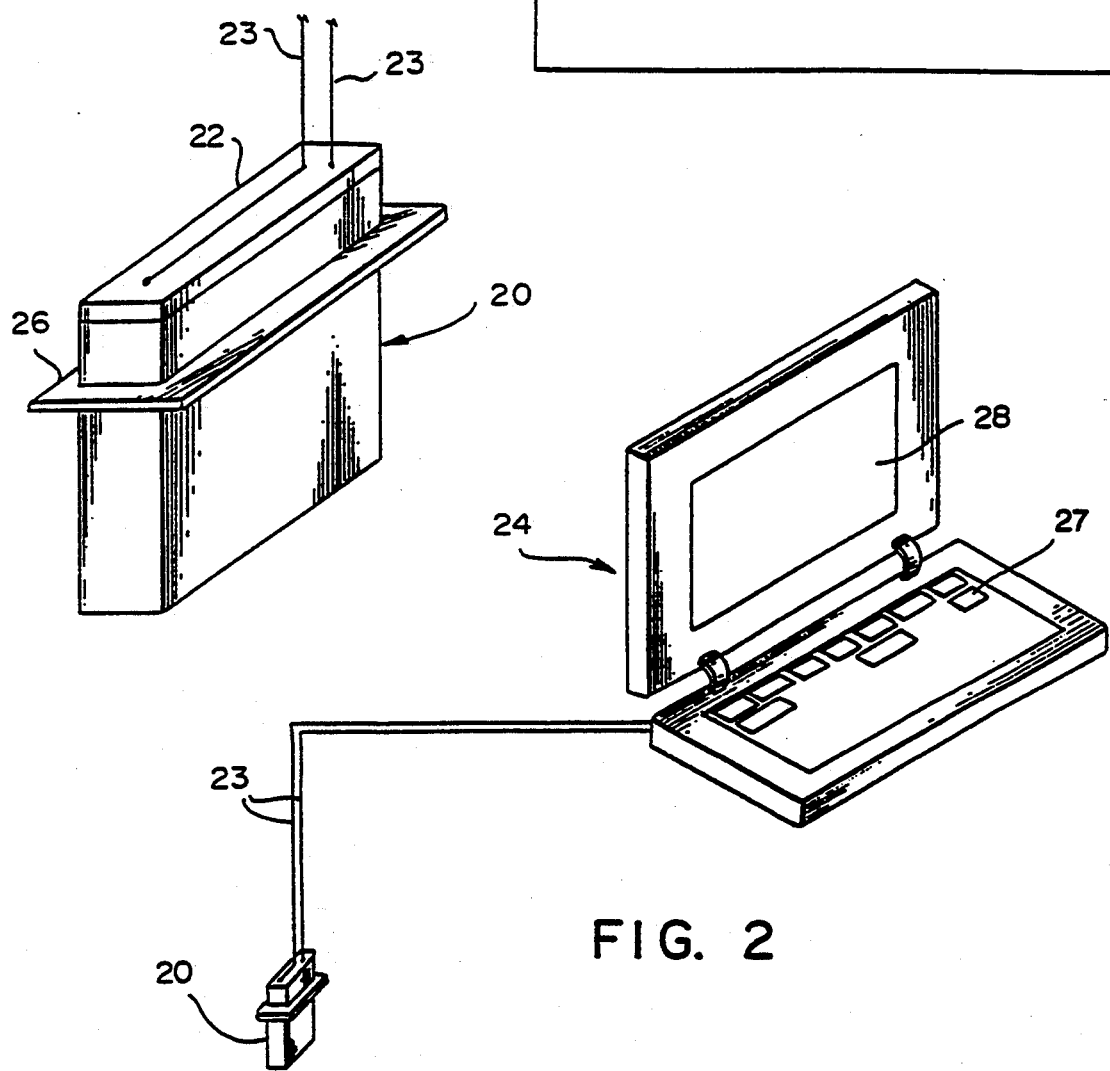

METHOD AND SYSTEM FOR CALIBRATING AN OPTICAL DENSITY MEASUREMENT APPARATUS

CROSS-REFERENCE TO RELATED APPLICATION

This application is a Continuation-in-Part of U.S. Ser. No. 793,627 filed Nov. 18, 1991, now abandoned.

TECHNICAL FIELD

This invention relates generally to optical systems and more particularly to a method and system for calibrating optical density measurement apparatus. In particular, the calibration system of this invention concerns light modulation by changing the transmission parameters of an optical element.

BACKGROUND ART

Optical information processing systems conventionally utilize a light source and a detector providing a photo-optical path. These systems are generally designed to acquire data about a medium placed within the photo-optical path and, for example, can be used for position sensing, color determination, and for measuring reflectivity and transmissivity of the medium.

Optical intensity mapping devices that sense variations in optical density or light scattering of a medium are used in analytical chemistry for measuring critical micelle concentration by detergents, fatty acids and phospholipids. Similar photodetector instruments have been applied to analytical biochemistry for example, in blood clotting time measuring apparatus. These apparatus generally employ a sensor for determining increases in optical density and provide a signal proportional to the optical properties. Typical devices for optical blood analysis are illustrated in U.S. Pat. Nos. 4,876,069; 4,720,787; and 4,775,237.

With regard to devices for monitoring blood coagulation, plasma from a blood specimen is usually combined with a prescribed amount of chemical reagents which precipitate clotting. As the clotting progresses, the optical density of the specimen increases. A graphic history of the specimen's optical density over time is referred to as a "clot signature." Characteristics of a patient's clot signature provide clinicians with diagnostic information about the patient's medical condition.

Currently, the process for the measurement of blood coagulation is subject to variables which must be controlled or standardized if the measurement process is to yield valid and consistent results. In regard to optical coagulation sensing instrumentation, the apparatus is calibrated by combining reagents with a sample of control plasma or standard solution and then comparing the resulting "clot signature" with a prescribed norm or benchmark. However, if the control plasma and/or patient plasma produces an irregular or abnormal "clot signature," it is difficult to isolate the source of this inconsistency. The problem may lie in the composition of the control plasma, the reagent solutions, the hydraulic system delivering the reagent solutions or the photodetector system. The diagnosis of the irregularities in the test results can be expensive and a time-consuming procedure involving for example, the verification of the composition of the control plasma, the reagent solutions or confirmation as to the accuracy of the hydraulic system or photodetector system. Frequently, a technician must be summoned to examine the apparatus and to determine the source of the problem. This often results in "downtime" or a cessation of a medical facility's blood analysis program until the malfunction is remedied. Furthermore, it is impractical for hospitals to purchase redundant blood analysis apparatus in view of the expense involved or to maintain an oversupply of reagent solutions in view of their perishability.

DISCLOSURE OF THE INVENTION

Briefly, the nature of this invention concerns a calibration system for optical density measurement apparatus that can emulate the change in optical density over a time interval corresponding to an established benchmark.

The purpose of the calibration system is to aid in the diagnosis and adjustment of the optical density measurement apparatus.

The calibration system relies upon a modulated electro-optical device wherein the optical transmittance parameters of the device are externally controlled by a programmable central processing unit as a function of time for simulating the time-course of optical density changes in a chemical process.

The electro-optical device is included as a component of a self-contained calibration system for use with the optical density measurement apparatus or alternatively can be included as an integral part of the measurement apparatus.

A feature of this invention is that the calibration system aids in locating sources of error when measuring the magnitude of light transmission by utilizing a physical process to generate a transmittance change which closely duplicates the biochemical calibration process which uses a standard solution.

In one embodiment of the invention the electro-optical device is a single cell liquid crystal display (LCD) commonly referred to a light valve. A computer-generated digital control signal is converted to an analog signal to provide an AC voltage of selected magnitude and frequency to drive the light valve.

In a second and preferred embodiment of the invention, the electro-optical device is a matrix-array type or graphic liquid crystal display module. Computer generated commands are provided to a display controller for activating the appropriate pixels of the graphic LCD to emulate the standard solution.

Having thus summarized the invention, it will be seen that it is an object thereof to provide an improved calibration device for optical density measurement apparatus of the general character described herein.

Specifically, it is an object of the present invention to provide a calibration system for optical density measurement apparatus utilizing a graphic LCD for selective modulation of light transmission.

Another object of this invention is to provide a calibration system for optical density measurement apparatus utilizing a graphic LCD for duplicating predetermined light transmission values corresponding to established norms.

Yet another object of this invention is to provide a calibration system utilizing a graphic LCD which is readily compatible with currently available optical density measurement apparatus.

Yet another object of this invention is to provide a calibration device which utilizes a graphic LCD in order to more realistically replicate in geometry the physical process being simulated.

Other objects, features and advantages of the invention will in part be obvious and will in part be pointed out hereinafter.

With these ends in view, the invention finds embodiments in certain combinations of elements and arrangements of parts by which the objects aforementioned and certain other objects are hereinafter attained, all as more fully described with reference to the accompanying drawings and the scope of which is more particularly pointed out in the appended claims.

BRIEF DESCRIPTION OF THE DRAWINGS

A more complete understanding of the present invention may be had from the following detailed description which should be read in conjunction with the drawings in which:

FIG. 1 is a schematic diagram of a calibration device of this invention showing a central processing unit, a digital-to-analog converter and an electro-optical light valve positioned within a photo-optical path of an optical density measurement apparatus;

FIG. 2 is a perspective view illustrating a portable computer which includes a digital-to-analog converter and provides a user interface;

FIG. 3 is a perspective view, to an enlarged scale, of the light valve showing the support collar for retaining the light valve within the optical density measurement apparatus;

DETAILED DESCRIPTION OF THE INVENTION

Figure 4:
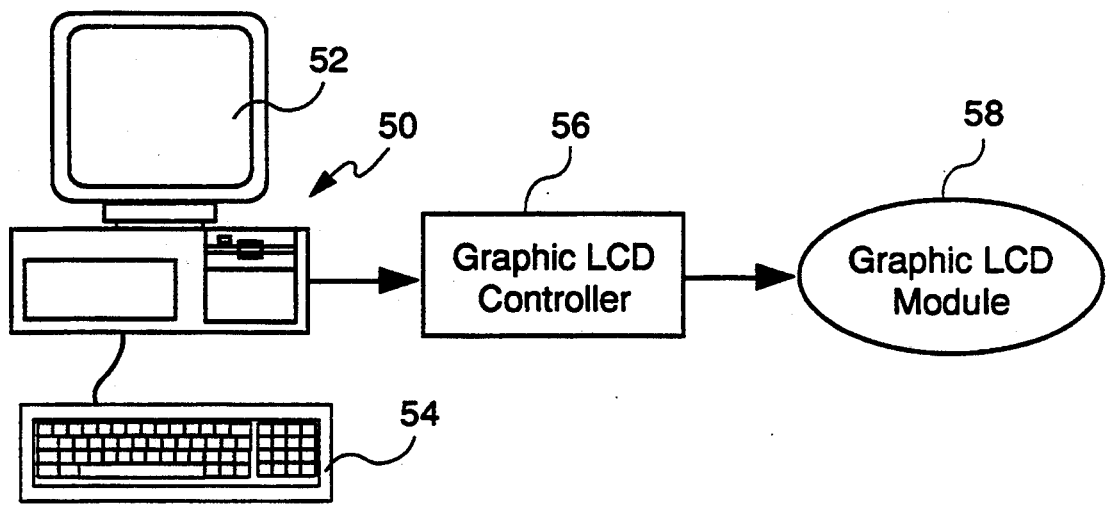
FIG. 4 is a partial block diagram of a second and preferred embodiment of the invention utilizing a graphic LCD module controlled from a personal computer.

Referring now in detail to the drawings, and initially to FIG. 1, the reference numeral 10 refers generally to a calibration device in accordance with this invention as applied to an optical density measurement apparatus 12 such as an optical blood analysis device.

The apparatus 12 includes a light source 14 and a photodetector 16 defining an optical path 18. The transmissivity of a specimen placed within the optical path 18 can, for example, be determined by a signal output generated by the photodetector 16.

In an apparatus that measures blood clotting times, for example, the KoaguLab 60-S (distributed by Ortho Diagnostic Systems, Inc., a subsidiary of Johnson & Johnson Co.), a "standard solution" is positioned within a measuring chamber 19 that intercepts the optical path 18. The "standard solution" is utilized for mapping a reference or "clot signature." The analog voltage signal generated by the photodetector 16 is converted to digital values. The time-voltage data is stored in computer memory and by the maximum clotting end point, the computer has accumulated an array of voltage versus reaction time data which can be displayed graphically as a "clot signature."

A light transmission modulation unit, preferably a light valve 20, is used to produce a physical emulation of the change in density of the "standard solution" over a predetermined time interval. In this embodiment, a twisted nematic field effect LCD (as available from Standish Industries, Lake Mills, Wis.), has been utilized. The light valve 20 operates on alternating current following a square wave pattern with a voltage of between 0 to $+/-5$ volts and a frequency of between 30–100 Hz. Light transmission can be selectively varied from maximum transparency at 0 volts, to maximum opacity at $+/-5$ volts. By way of example, the dimensions of the light valve in this embodiment are 1.35 inches in length, 0.750 inches in height and 0.15 inches in width. These dimensions can be varied to correspond with the size of the measuring chamber 19.

With reference to FIGS. 2 and 3, the light valve 20 further includes a single side, top mounted contact ledge 22 which can be hardwired, as illustrated by a line 23, to a programmable portable computer 24 or an equivalent signal generating device. A collar 26 projects peripherally from the light valve 20 to provide support when the light valve 20 is positioned in the optical path 18. The computer 24 has a user interface, such as keys 27 and a display screen 28.

It should be noted that parameters which define the "clot signature" to be emulated are input to the computer 24. These input parameters are: blank time (elapsed time before the simulated clotting reaction begins), start transmittance level (initial opacity of light valve), end transmittance level (opacity of light valve corresponding to completion of simulated clotting), ramp time, the elapsed time between end of blank time and the achievement of the end transmittance level, and plateau time, the time during which the end transmittance level is maintained. The graphical representation of the clot signature will appear as a sloped line corresponding to the change in opacity, as measured along a vertical "y" axis, vs. time, as measured along a horizontal "x" axis.

With this information, the desired time course is fully defined. The crystal clock of the computer 24 provides an accurate time signal for a software counter which is read by the computer 24. The computer 24 further calculates the voltage level to be applied to the light valve 20, depending on the transmittance-voltage characteristic of the light valve 20 and the desired time course of optical density change. The computer 24 also systematically outputs commands corresponding to the representative "clot signature." The digital output command are converted to an analog voltage signal by a converter 30 to drive the light valve 20. The computer 24, by virtue of being programmed with a voltage-optical density characteristic for the particular light valve 20, and the speed of response of the light valve 20 to voltage changes can generate any desired time course of change in optical density in order to provide a selected "clot signature" within the possible range of contrast change of the light valve 20. The level of voltage required to produce a given level of opacity in the light valve 20 may vary by as much as 100 mv. Therefore offset and alignment variables which permit calibration of each light valve 20 can be built into the operating program.

By way of reference, the digital-to-analog converter 30 as used herein is an expansion board adapted for use with an IBM PC compatible 286, 386, or 486 computer. The expansion board employed can provide a voltage output range of −5 to +5 volts. The vendors of the converter 30 provide a software interface which permits the converter 30 to be controlled by commands which are issued from within a program written in "C" language running on the computer 24. The "C" commands specify a voltage magnitude and sign (+ or −) and the program is designed to systematically cause the D/A converter 30 to output a square wave with a voltage varying from 0 to +/−5 volts. At any given absolute value of voltage corresponding to desired opacity, the program commands the D/A 30 to alternate between positive and negative voltages, to insure an alternating voltage signal.

Based on the previously discussed input parameters—blank time, start transmittance level, end transmittance level, ramp time, and plateau time, the "C" program calculates the voltage output to the light valve 20 at any given time. Furthermore, at any given absolute value of voltage corresponding to a desired opacity, the "C" program sends the appropriate command to the D/A converter 30 to cause it to switch between positive and negative voltage for simulating an alternating square wave voltage. An alternating voltage is required to avoid depolarization of the liquid crystal material in the light valve 20 which would occur with direct current.

It should further be noted that the computer 24 suitable for this invention can be an IBM PC compatible computer, such as a Toshiba 386 SX or can be designed with a custom programmable circuit for a dedicated device.

As previously discussed, the light valve 20 includes the collar 26 for seating within the optical density measurement apparatus 12. For example, if the light valve 20 is employed with the KoaguLab 60-S apparatus, guideways are provided for accepting cuvette trays containing the plasma for both the "standard solution" and for test analysis. The light valve 20 is preferably sized to correspond to the dimensions of the cuvettes which are utilized with that device.

Figure 5:
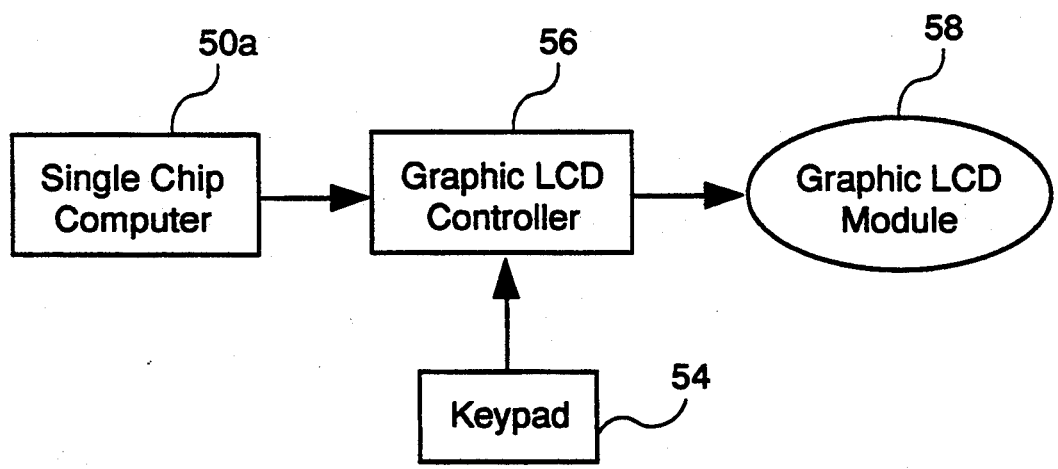
FIG. 5 is a block diagram of the second embodiment of the invention wherein the graphic LCD module is controlled from a single chip computer.

FIG. 4 shows a second and preferred embodiment of the invention in which the electro-optical device is a graphic LCD module 58 which includes a plurality of individually selectable elements or pixels forming a matrix having M rows and N columns. The module 58 may be of the type generally referred to as an instrument size LCD with, for example, 64×240 pixel graphics. A variety of such displays are available from Toshiba and other companies and are commonly controlled by the Toshiba T6963C which is a dot matrix LCD pixel driver. The module 58 is controlled from a microcomputer 50, with display 52 and keyboard 54, which provide the necessary commands to a graphic LCD controller 56 such as the CY325 from Cybernetic Micro Systems, Inc. The CY325 is a high level graphic LCD controller which permits the system designer and programmer to control the LCD with high-level commands rather than low-level pixel-oriented commands required by pixel drivers such as the T6963C. Alternatively, the microcomputer 50 may be replaced with a microcontroller 50a such as a member of the Intel 8051 family as shown in FIG. 5. As with the embodiment of FIGS. 1-3, the software running on the microcomputer 50 or microcontroller 50a creates a data entry screen or form which solicits the input parameters described above. However, unlike the previous embodiment this embodiment allows the electro-optical device which undergoes the transmittance change to also serve to display the data entry screens.

Figure 6:
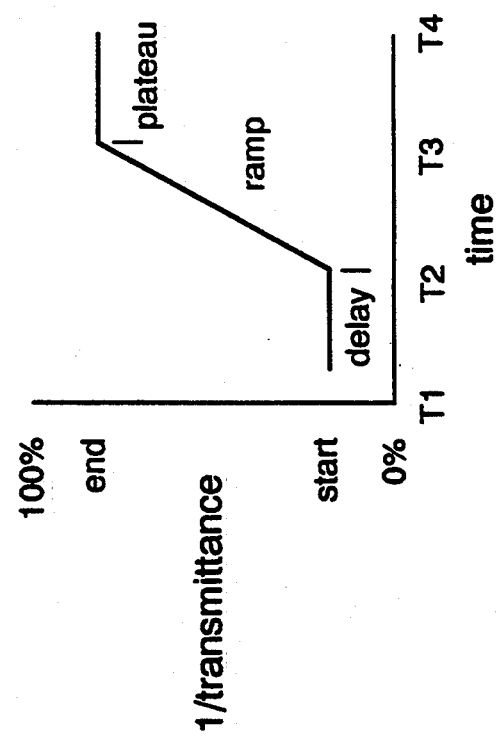
FIG. 6 is a graph of a typical simulated clot signature.

Referring now to FIG. 6 a typical simulated clot signature is shown. The parameter "blank time" defines the time delay interval between the beginning of the calibration run at time T1 and the point at which simulated clotting reaction begins at time T2. The "elapsed time" parameter corresponds to the interval between times T2 and T3 wherein the transmittance of the matrix panel is altered from the value input for the start transmittance level to the value input for the end transmittance level. A "plateau time" interval parameter defines the interval from time T3 to T4 wherein the transmittance level is maintained at the end transmittance level.

While the simulated clot signature in FIG. 6 is shown as changing linearly over time, this is by way of example only. If desired, a time course of transmittance levels extending between a start and end transmittance levels which would simulate a non-linear clot signature may be entered by the operator. The matrix of pixels permits more accurate control of the levels of transmittance and geometry of transmittance changes of the graphic LCD module 58 than the single cell of the embodiment of FIGS. 1-3 and therefore is capable of providing a more realistic replication of the clotting process being simulated. For example, by manipulating the sequence of pixel activation, a clot could be simulated that begins from the bottom of the cuvette and progresses upward and outward. A simple light valve is homogenous in opacity, and cannot simulate geometrical spreading of the actual biochemical process. In addition, the graphic LCD module 58 can simulate variation in levels of reagent filling of the cuvettes by placing the pixel boundary at different heights. Therefore the second embodiment can simulate more realistic changes in transmittance.

For the embodiment of FIGS. 4-5, experiments are performed to determine the pixel activation geometry necessary to elicit the desired standard clot signatures. Generally speaking as the number of pixel activations increase, the display becomes more opaque. Once the pixel activation geometry sequence is determined, the computer language commands are written that will cause the graphic LCD controller 56 to produce this sequence. The computer language commands are communicated over an RS-232 connection from the microcomputer 52 to the controller 56. The controller 56 provides low level pixel oriented commands to the Toshiba T6963C pixel driver which drives the graphic LCD module 58.

Figure 7:
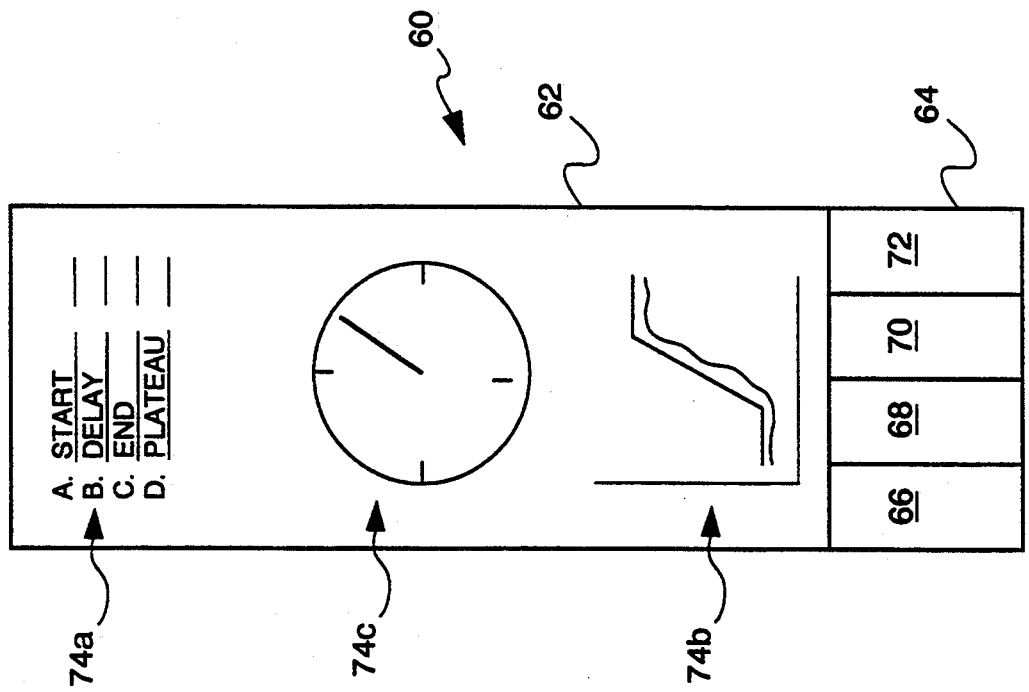
FIG. 7 is a layout of the graphic LCD module including both a user interface portion and a light transmittance varying portion and which is particularly suitable, as configured, for use with a four channel coagulation machine.

FIG. 7 shows a preferred layout of the graphic LCD module 58. The module 58 is preferably a single panel generally designated 60 formed of an upper portion 62 and lower portion 64. In contrast to the upper portion 62, which possesses the usual reflective backing of the conventional instrument type graphic LCD, the lower portion 64 does not include a reflective backing in order to allow the direct passage of light therethrough. The panel 60 is approximately 2"×6" and is preferably sized to be similar in width to a cuvette so that it fits readily into the testing compartment of the clot detection system. The lower portion 64 performs the variable light transmittance function to emulate the clot signature while the upper portion 62 performs a user interface function. Both functions are under the ultimate control of the microcomputer 50. As shown the lower portion 64 comprises four separately controllable windows or displays 66–72 suitable for calibrating the four channels respectively of the aforementioned Koagulab 60S apparatus. Each of the pixels in the four quadrants can be controlled separately by the graphic LCD controller 56 and can be used to calibrate the four channel Koagulab 60S without modification of the software which controls the Koagulab 60S. This is an advantage over the use of the single light valve of FIGS. 1–3 which without modification of the Koagulab 60S software would calculate a different clotting time for each channel. This would be an incorrect determination of clotting time which is the most essential parameter in medical diagnosis of blood clotting. Moreover, a single cell light valve will degenerate with use over time causing the level of opacity change associated with a given input voltage to be lower than when the light valve was new. A single cell light valve will itself need periodic recalibration, requiring software modification, or will have to be replaced. In the preferred embodiment using the pixel array approach, each pixel is either on or off, so that variation of overall opacity over time is minimized. Furthermore, unlike the embodiment of FIGS. 1–3, a D/A converter is not required.

As indicated, the upper portion 62 provides a user interface so that information may be conveyed to the operator in the form of alpha-numeric instructions or status information as indicated at region 74a. Once the parameters are entered, the module 58 displays to the operator the simulated clot signature of FIG. 6 in graphic form as indicated at region 74b for verification of the test to be run. Where the coagulation apparatus provides an output of the calibration run data, the measured data is displayed in the region 74b for comparison with the simulated signature. This will give the test operator immediate visual feedback of the performance of the coagulation apparatus. Additionally, the time course status of the calibration run is displayed in the region 74c in the form of a graphic timer. Since the upper portion of the LCD module 58 provides a user interface the apparatus of FIG. 5 may be configured as a small portable device approximately the size of a hand-held calculator. The second embodiment lends itself to miniaturization because all of the functions performed by the portable computer display can be performed by the graphic LCD module.

Figure 8:
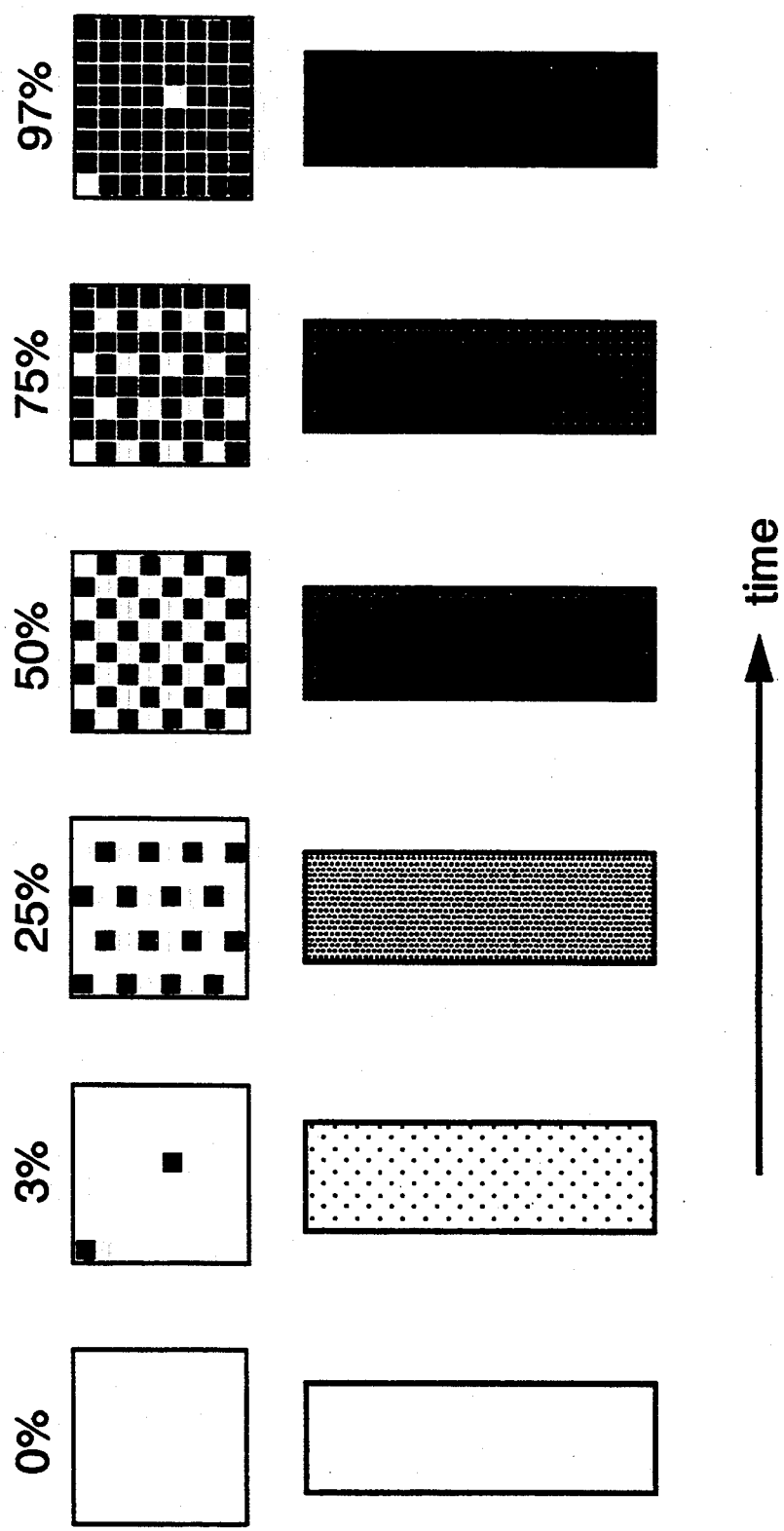
FIG. 8 illustrates how pixel selection and activation may be used to vary the overall transmittance of the graphic LCD module.

Referring now to FIG. 8, the manner in which the graphic LCD module 58 is controlled to achieve various levels of opacity from maximum transmission of light to 97% blockage of light transmission is graphically pictured. The lower segment of FIG. 8 represents one of the windows 66–72 of the lower portion 64 of the panel 60 while the upper segment of FIG. 8 represents one of the plurality of 8×8 pixel arrays which together form one of the windows 66–72. Together the arrays provide 256 discrete levels of transmission. Thus, by activating 2 of the 64 pixels in each of the plurality of 8×8 pixel arrays an overall relative opacity level of 3% can be achieved. Similarly, by activating 62 of the 64 pixels in each array, an overall relative opacity level of 97% can be achieved. The specific pixel activation geometry for achieving a desired opacity is dependent on the specific graphic LCD module 58 utilized and is based on experimentation. The accuracy and simplicity with which the graphic LCD module 58 can be controlled is significantly greater than that permitted by the embodiment of FIGS. 1–3 where a non-linear relationship exists between the voltage applied to the light valve and the resulting opacity.

Figure 9A:
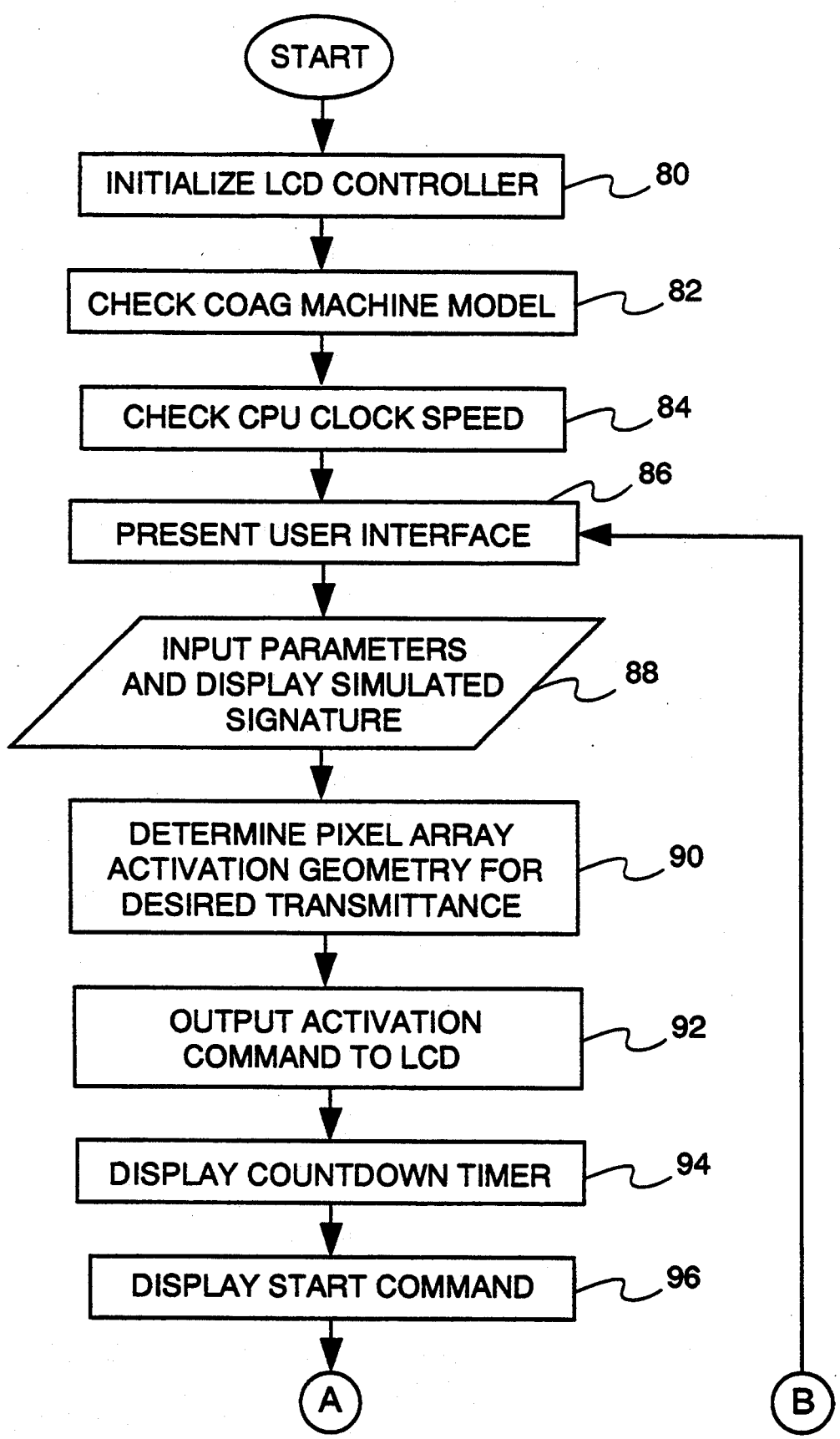
FIG. 9a, 9b, and 9c together is a flow chart of the calibration process of the present invention.
Figure 9B:
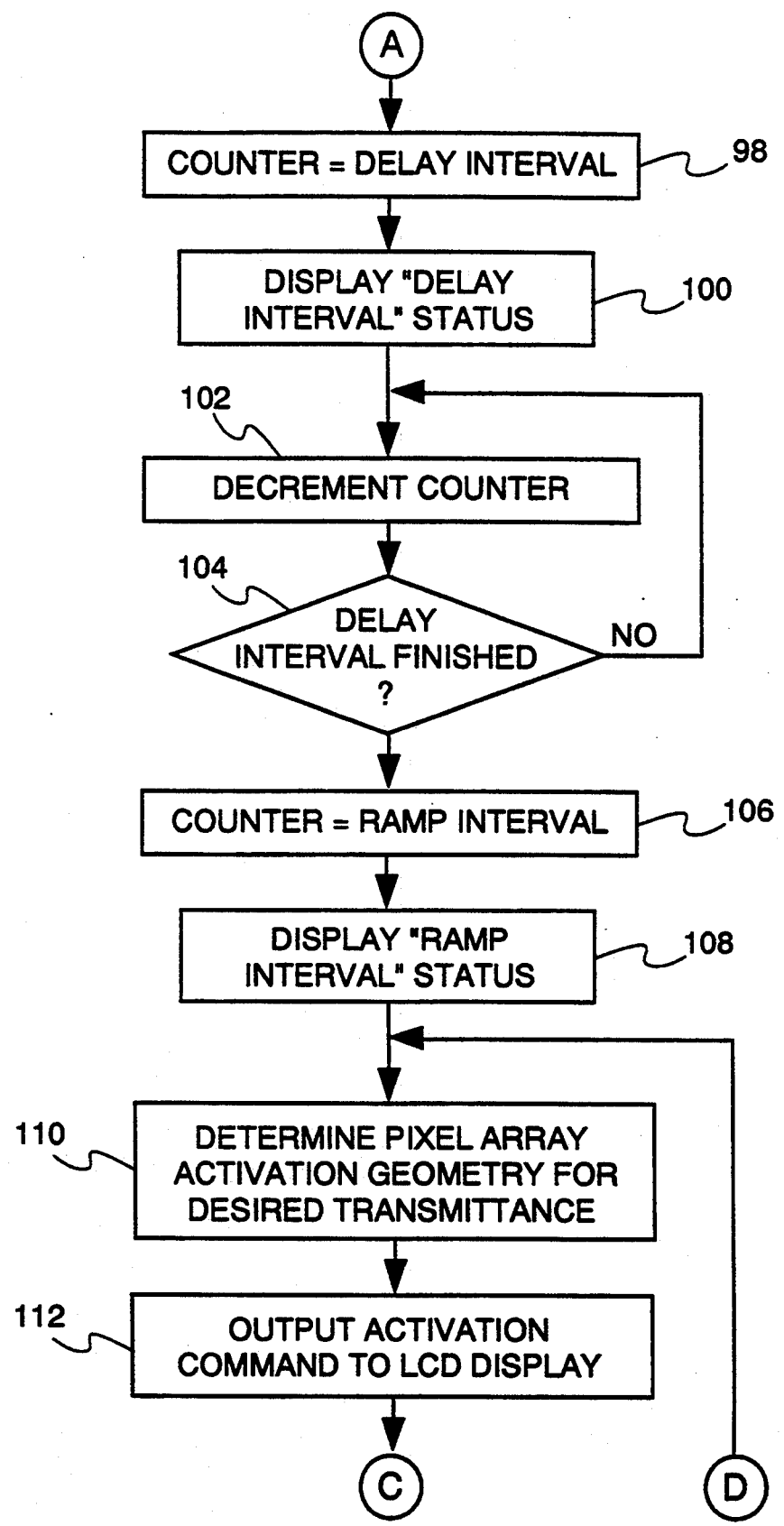
Figure 9C:
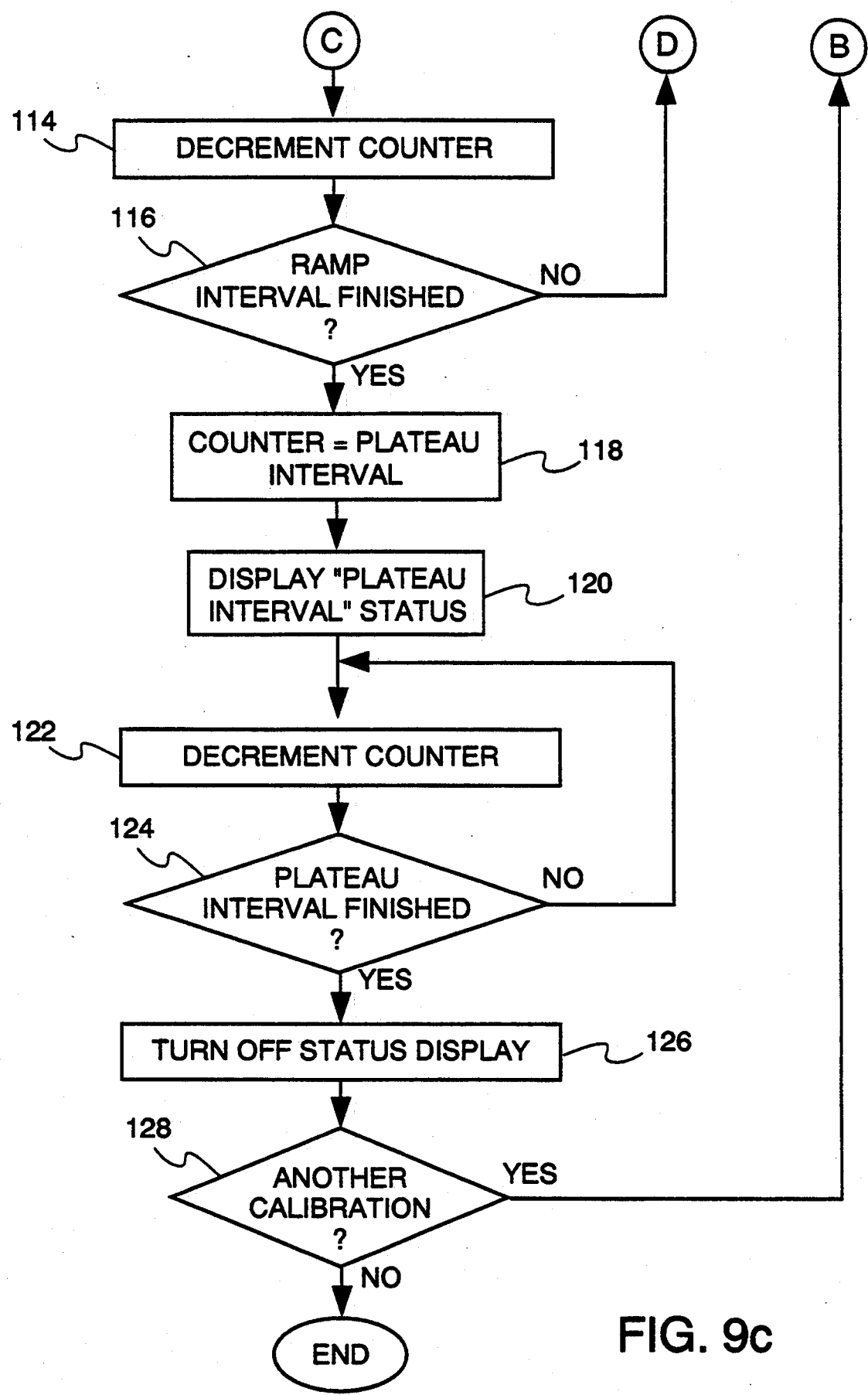

Referring now to FIG. 9 a flow chart of the program running on computer 50 for controlling the generation of the simulated clot signature will now be described. In order to use the calibration device on a variety of different coagulation measurement machines it may be desirable to store in the memory of the computer 50, information regarding the physical arrangement and characteristics of the light source and photodetector of the various machines to be calibrated. This information may include the light source beam size, light intensity, geometric layout, and photodetector characteristics so that these parameters can be taken into account in generating the pixel activation geometry. After the graphic LCD controller is initialized at 80, this information can then be accessed in response to identification of the coagulation machine model type at 82. Alternatively, if the calibration device is built into the coagulation machine, this information would be coded into the calibration software. At 84 the clock speed of the CPU of the computer 50 is provided as a time base input to the program. At 86, the program presents to the operator a user interface screen which solicits the input parameters described previously in connection with FIG. 6. At 88 these parameters are input and displayed in the region 74a and the simulated clot signature is graphed, based on the input parameters, and displayed in the region 74b. At 90, the pixel array geometry needed to provide the desired start transmittance is determined and at 92 the commands to the graphic LCD module 58 are output by the controller 56. The timer which is located on the upper portion of the panel 60 in FIG. 7 is displayed at 94 and the command to start the coagulation machine test procedure is displayed at 96. Alternatively, where the calibration device is incorporated in the coagulation machine, the coagulation machine calibration test procedure would be automatically started. The coagulation machine performs a number of timed functions such as reagent dispensation, sample cooling, sample cuvette incubation, and movement of the sample between the light source and photodetectors. The combined time of these processes makes up a time interval previously referred to as the delay interval in FIG. 6. At 98 a counter is set to the delay interval between T1 and T2 and status information such as "Delay Interval" is displayed at 100. The status information is displayed on the user interface in FIG. 7. The counter is decremented at 102, 104 until the delay interval is completed. At 106 the counter is set to the ramp duration time interval between T2 and T3 and the status information on the user interface is updated at 108 to display "Ramp Interval". At 110–116 the pixel array activation geometry is determined each time the counter is decremented. Corresponding activation commands are output to the graphic LCD module 58 which will produce the desired levels of transmittance over the ramp time interval between T2 and T3. As indicated at 118 the counter is then set to the plateau interval and the status information on the user interface is updated at 120 to display "Plateau Interval". At 122, 124 the counter is decremented to zero while maintaining the pixel array activation geometry last calculated during the ramp interval. When the plateau interval has expired the status display is turned off at 126, the decision block 128 is entered and a new calibration procedure is either performed or the program is ended.

Although the above description referred specifically to blood analysis apparatus, it should be understood that the device of this invention is intended for use in calibrating other apparatus that measure changes in optical density as a function of time. In those cases, other parameters would be entered and other information would serve as feedback to the operator.

Having thus described the invention, there is claimed as new and desired to be secured by Letters Patent:

What is claimed is:

1. A calibration device for use with optical density measuring apparatus that measures the optical density of a sample located in an optical path defined between a light source and a photodetector, said calibration device comprising light modulation means having a matrix of addressable pixels, control means for activating predefined ones of said pixels at fixed times over a predetermined time interval to emulate the change in opacity which occurs in a standard sample.

2. The device defined in claim 1 wherein said light modulation means comprises a graphic liquid crystal display module.

3. The device defined in claim 2 wherein the module is of the supertwist nematic LCD type.

4. The device defined in claim 1 wherein the pixel activations establish a sequence of pixel geometries which causes a light transmittance change over the sequence time interval which emulates the change in optical density of clotting blood plasma.

5. A calibration device for use with optical density measuring apparatus that measures the optical density of a sample located in an optical path defined between a light source and a photodetector, said calibration device comprising a graphic display module having a matrix of addressable pixels, control means for activating a sequence of discrete pixels geometries for controlling the transmittance level of said light modulation means to emulate the change in opacity which occurs in a standard sample over the sequence time interval.

6. The invention defined in claim 5 wherein the sample is a blood sample and the module is a liquid crystal.

7. The device of claim 5 wherein the display module includes a first portion undergoing said change in opacity and a second portion for displaying information to an operator performing the calibration.

8. The device of claim 7 wherein said apparatus includes a plurality of channels for measuring the clotting of a plurality of blood samples and wherein the first portion comprises a plurality of individually controllable displays associated with respective ones of said channels.

9. The device of claim 8 wherein the second portion includes a graphical representation.

10. The device of claim 9 wherein the representation is a timing device.

11. The device of claim 10 wherein the representation also includes a simulated clot signature.

12. A computer implemented method of generating a clot signature utilizing a matrix type liquid crystal display, comprising the steps of:
inputting data representing a desired time course of transmittance levels between a start and an end transmittance level over a predetermined interval of time,
determining pixel array activation geometries of the display that will produce said desired time course of transmittance levels in said display over said predetermined time interval between said start and end transmittance levels and,
outputting pixel activation commands to said display to produce said time course of transmittance levels to simulate said clot signature.

13. The method as defined in claim 12 wherein the input data is displayed on one portion of the matrix type liquid crystal type display and said time course of transmittance levels is produced on a second portion of said display.

14. A computer implemented method of generating a clot signature utilizing a matrix type liquid crystal display, comprising the steps of:
inputting values of blank time, start transmittance level, end transmittance level, time interval between the start and end transmittance levels and a plateau time interval,
determining a pixel array activation geometry of the display that will produce the desired start transmittance level and outputting pixel activation commands to said display to achieve said activation geometry for the period of said blank time,
determining pixel array activation geometries of the display that will produce a predetermined variation in the transmittance level of said display over said time interval between said start and end transmittance levels and outputting pixel activation commands to said display to achieve said variation and,
outputting pixel activation commands to said display to maintain the activation geometry that produces the desired end transmittance level for the period of said plateau time interval.

* * * * *